(12) United States Patent
Morton et al.

(10) Patent No.: US 7,700,292 B2
(45) Date of Patent: Apr. 20, 2010

(54) ALLELIC FORM OF THE HMGA2 GENE PREDISPOSING WOMEN TO THE FORMATION OF LEIOMYOMAS

(75) Inventors: Cynthia Morton, Newton, MA (US); Jennelle Hodge, Brookline, MA (US); Karen Gross Huyck, Cambridge, MA (US)

(73) Assignee: The Bringham and Woman's Hospital, Inc., Boston, MA (US)

( * ) Notice: Subject to any disclaimer, the term of this patent is extended or adjusted under 35 U.S.C. 154(b) by 155 days.

(21) Appl. No.: 11/598,623

(22) Filed: Nov. 14, 2006

(65) Prior Publication Data

US 2007/0124828 A1 May 31, 2007

Related U.S. Application Data

(60) Provisional application No. 60/736,833, filed on Nov. 16, 2005.

(51) Int. Cl.
*C07H 21/04* (2006.01)
*C12Q 1/68* (2006.01)

(52) U.S. Cl. .................. 435/6; 435/91.1; 435/91.2; 536/23.1; 536/23.4

(58) Field of Classification Search ................. None
See application file for complete search history.

(56) References Cited

OTHER PUBLICATIONS

Ishwad et al. (Human Genetics, vol. 99, pp. 103-105, 1997).*
Borrmann et al. (Oncogene, vol. 22, pp. 756-760, 2003).*
Gross et al. (Genes, Chromosomes, & Cancer, vol. 38, pp. 68-79, 2003).*
Lucentini (The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Borrmann, et al., "Human *HMGA2* Promoter is Coregulated by a Polymorphic Dinucleotide (TC)-Repeat," *Oncogene* 22:756-760 (2003).
Hauke, et al., "Extensive Expression Studies Revealed a Complex Alternative Splicing Pattern of the *HMGA2* Gene," Biochim. Biophys. Acta. 1729:24-31 (2005).
Hess, et al., "Chromosomal Translocations in Benign Tumors: The HMGI Proteins," *Am. J. Clin. Pathol.* 109:251-261 (1998).
Ishwad, et al., "The High Mobility Group I-C Gene (HMGI-C): Polymorphism and Genetic Localization," *Hum. Genet.* 99:103-105 (1997).
Ligon, et al., "Genetics of Uterine Leiomyomata," *Genes Chromosomes Cancer* 28:235-245 (2000).
Manfioletti, et al., "cDNA Cloning of the HMGI-C Phosphoprotein, a Nuclear Protein Associated With Neoplastic and Undifferentiated Phenotypes," *Nucl. Ac. Res.* 19:6793-6797 (1991).
Reeves, et al., "HMGI/Y Proteins: Flexible Regulators of Transcription and Chromatin Structure," *Biochim. Biophys. Acta.* 1519:13-29 (2001).
Schoenmakers, et al., "Identification, Molecular Cloning, and Characterization of the Chromosome 12 Breakpoint Cluster Region of Uterine Leiomyomas," *Genes Chromosomes Cancer* 11:106-118 (1994).
Zhou, et al., "Genomic Structure and Expression of the Murine *Hmgi-c* Gene," *Nucl. Ac. Res.* 24:4071-4077 (1996).
International Search Report for PCT/US06/44172 filed Nov. 14, 2006.
Written Opinion of the International Searching Authority for PCT/US06/44172 filed Nov. 14, 2006.
Hodge, et al., "Uterine leiomyomata and decreased height: a common *HMGA2* predisposition allele" Hum. Genet (published online, Jan. 9, 2009).
International Preliminary Examination Report for PCT/US06/44172 filed Nov. 14, 2006.

\* cited by examiner

*Primary Examiner*—Jeanine A Goldberg
(74) *Attorney, Agent, or Firm*—Law Office of: Michael A. Sanzo, LLC

(57) ABSTRACT

The present invention is directed to diagnostic assays that can be used to determine if a woman carries an allelic form of the HMGA2 gene that predisposes her to the formation of fibroid tumors. The invention also encompasses vectors containing this allele, cells transformed with these vectors and transgenic animals that carry at least one copy of the allele.

20 Claims, 6 Drawing Sheets

```
   1 cttgaatctt ggggcaggaa ctcagaaaac ttccagcccg ggcagcgcgc gcttggtgca
  61 agactcagga gctagcagcc cgtcccctc cgactctccg gtgccgccgc tgcctgctcc
 121 cgccaccta ggaggcgcgg tgccacccac tactctgtcc tctgcctgtg ctccgtgccc
 181 gaccctatcc cggcggagtc tccccatcct cctttgcttt ccgactgccc aaggcacttt
 241 caatctcaat ctcttctctc tctctctctc tctctctctc tctctctctc tctctctctc
 301 tctctctctc gcagggtggg gggaagagga ggaggaattc tttccccgcc taacatttca
 361 agggacacaa ttcactccaa gtctcttccc tttccaagcc gcttccgaag tgctcccggt
 421 gcccgcaact cctgatccca acccgcgaga ggagcctctg cgacctcaaa gcctctcttc
 481 cttctccctc gcttccctcc tcctcttgct acctccacct ccaccgccac ctccacctcc
 541 ggcacccacc caccgccgcc gccgccaccg gcagcgcctc ctcctctcct cctcctcctc
 601 ccctcttctc tttttggcag ccgctggacg tccggtgttg atggtggcag cggcggcagc
 661 ctaagcaaca gcagccctcg cagcccgcca gctcgcgctc gccccgccgg cgtccccagc
 721 cctatcacct catctcccga aaggtgctgg gcagctccgg ggcggtcgag gcgaagcggc
 781 tgcagcggcg gtagcggcgg cgggaggcag gatgagcgca cgcggtgagg gcgcggggca
 841 gccgtccact tcagcccagg gacaacctgc cgccccagcg cctcagaaga gaggacgcgg
 901 ccgccccagg aagcagcagc aagaaccaac cggtgagccc tctcctaaga gacccagggg
 961 aagacccaaa ggcagcaaaa acaagagtcc ctctaaagca gctcaaaaga aagcagaagc
1021 cactggagaa aaacggccaa gaggcagacc taggaaatgg ccacaacaag ttgttcagaa
1081 gaagcctgct caggaggaaa ctgaagagac atcctcacaa gagtctgccg aagaggacta
1141 gggggcgcca acgttcgatt tctacctcag cagcagttgg atcttttgaa gggagaagac
1201 actgcagtga ccacttattc tgtattgcca tggtctttcc actttcatct ggggtgggt
1261 ggggtggggt ggggagggg ggggtggggt gggagaaat cacataacct taaaaaggac
1321 tatattaatc accttctttg taatcccttc acagtcccag gtttagtgaa aaactgctgt
1381 aaacacaggg gacacagctt aacaatgcaa ctttaatta ctgtttctt ttttcttaac
1441 ctactaatag tttgttgatc tgataagcaa gagtgggcgg gtgagaaaaa ccgaattggg
1501 tttagtcaat cactgcactg catgcaaaca agaaacgtgt cacacttgtg acgtcgggca
1561 ttcatatagg aagaacgcgg tgtgtaacac tgtgtacacc tcaaatacca ccccaaccca
1621 ctccctgtag tgaatcctct gtttagaaca ccaaagataa ggactagata ctactttctc
1681 tttttcgtat aatcttgtag acacttactt gatgatttt aactttttat ttctaaatga
1741 gacgaaatgc tgatgtatcc tttcattcag ctaacaaact agaaaaggtt atgttcattt
1801 ttcaaaaagg gaagtaagca acaaatatt gccaactctt ctatttatgg atatcacaca
1861 tatcagcagg agtaataaat ttactcacag cacttgtttt caggacaaca cttcattttc
1921 aggaaatcta cttcctacag agccaaaatg ccatttagca ataaataaca cttgtcagcc
1981 tcagagcatt taaggaaact agacaagtaa aattatcctc tttgtaattt aatgaaaagg
2041 tacaacagaa taatgcatga tgaactcacc taattatgag gtgggaggag cgaaatctaa
2101 atttcttttg ctatagttat acatcaattt aaaaagcaaa aaaaaaaag ggggggcaa
2161 tctctctctg tgtctttctc tctctctctt cctctccctc tctcttttca ttgtgtatca
2221 gtttccatga aagacctgaa taccacttac ctcaaattaa gcatatgtgt tacttcaagt
2281 aatacgtttt gacataagat ggttgaccaa ggtgcttttc ttcggcttga gttcaccatc
2341 tcttcattca aactgcactt ttagccagag atgcaatata tccccactac tcaatactac
2401 ctctgaatgt tacaacgaat ttacagtcta gtacttatta catgctgcta tacacaagca
2461 atgcaagaaa aaaacttact gggtaggtga ttctaatcat ctgcagttct ttttgtacac
2521 ttaattacag ttaaagaagc aatctcctta ctgtgtttca gcatgactat gtattttct
2581 atgttttttt aattaaaaat ttttaaaata cttgtttcag cttctctgct agatttctac
2641 attaacttga aaatttttta accaagtcgc tcctaggttc ttaaggataa ttttcctcaa
2701 tcacactaca catcacacaa gatttgactg taatatttaa atattaccct ccaagtctgt
2761 acctcaaatg aattctttaa ggagatggac taattgactt gcaaagacct acctccagac
2821 ttcaaaagga atgaacttgt tacttgcagc attcatttgt tttttcaatg tttgaaatag
2881 ttcaaactgc agctaaccct agtcaaaact attttttgtaa aagacatttg atagaaagga
2941 acacgttttt acatactttt gcaaaataag taaataataa ataaaataaa agccaacctt
3001 caaagaaact tgaagctttg taggtgagat gcaacaagcc ctgcttttgc ataatgcaat
3061 caaaaatatg tgttttaag attagttgaa tataagaaaa tgcttgacaa atattttcat
3121 gtattttaca caaatgtgat ttttgtaata tgtctcaacc agatttattt taaacgcttc
3181 ttatgtagag ttttatgcc tttctctcct agtgagtgtg ctgactttt aacatggtat
3241 tatcaactgg gccaggaggt agtttctcat gacggctttt gtcagtatgg cttttagtac
```

Figure 1

```
3301 tgaagccaaa tgaaactcaa aaccatctct cttccagctg cttcagggag gtagtttcaa
3361 aggccacata cctctctgag actggcagat cgctcactgt tgtgaatcac caaaggagct
3421 atggagagaa ttaaaactca acattactgt taactgtgcg ttaaataagc aaataaacag
3481 tggctcataa aaataaaagt cgcattccat atctttggat gggccttttta gaaacctcat
3541 tggccagctc ataaaatgga agcaattgct catgttggcc aaacatggtg caccgagtga
3601 tttccatctc tggtaaagtt acacttttat ttcctgtatg ttgtacaatc aaaacacact
3661 actacctctt aagtcccagt atacctcatt tttcatactg aaaaaaaaag cttgtggcca
3721 atggaacagt aagaacatca taaaatttt atatatatag tttatttttg tgggagataa
3781 attttatagg actgttcttt gctgttgttg gtcgcagcta cataagactg gacatttaac
3841 ttttctacca tttctgcaag ttaggtatgt ttgcaggaga aaagtatcaa gacgtttaac
3901 tgcagttgac tttctccctg ttcctttgag tgtcttctaa ctttattctt tgttctttat
3961 gtagaattgc tgtctatgat tgtactttga atcgcttgct tgttgaaaat atttctctag
4021 tgtattatca ctgtctgttc tgcacaataa acataacagc ctctgtgatc cccatgtgtt
4081 ttgattcctg ctctttgtta cagttccatt aaatgagtaa taaagtttgg tcaaaacaga
4141 aaaaaaaaaa
```

Figure 1 (cont.)

```
   1 cttgaatctt ggggcaggaa ctcagaaaac ttccagcccg ggcagcgcgc gcttggtgca
  61 agactcagga gctagcagcc cgtcccctc cgactctccg gtgccgccgc tgcctgctcc
 121 cgccaccta ggaggcgcgg tgccacccac tactctgtcc tctgcctgtg ctccgtgccc
 181 gaccctatcc cggcggagtc tccccatcct cctttgcttt ccgactgccc aaggcacttt
 241 caatctcaat ctcttctctc tctctctctc tctctctctc tctctctctc tctctctctc
 301 tctctctctc gcagggtggg gggaagagga ggaggaattc tttccccgcc taacatttca
 361 agggacacaa ttcactccaa gtctcttccc tttccaagcc gcttccgaag tgctcccggt
 421 gcccgcaact cctgatccca acccgcgaga ggagcctctg cgacctcaaa gcctctcttc
 481 cttctccctc gcttccctcc tctcttgct acctccacct ccaccgccac ctccacctcc
 541 ggcacccacc caccgccgcc gccgccaccg gcagcgcctc ctcctctcct cctcctcctc
 601 ccctcttctc tttttggcag ccgctggacg tccggtgttg atggtggcag cggcggcagc
 661 ctaagcaaca gcagccctcg cagcccgcca gctcgcgctc gccccgccgg cgtcccagc
 721 cctatcacct catctcccga aaggtgctgg gcagctccgg ggcggtcgag gcgaagcggc
 781 tgcagcggcg gtagcggcgg cgggaggcag gatgagcgca cgcggtgagg gcgcggggca
 841 gccgtccact tcagcccagg gacaacctgc cgccccagcg cctcagaaga gaggacgcgg
 901 ccgccccagg aagcagcagc aagaaccaac cggtgagccc tctcctaaga gacccagggg
 961 aagacccaaa ggcagcaaaa acaagagtcc ctctaaagca gctcaaaaga aagcagaagc
1021 cactggagaa aaacggccaa gaggcagacc taggaaatgg gacaatctac taccaagaac
1081 cagctccaag aagaaaacat ctctgggaaa cagtaccaaa aggagtcact gaattgtcat
1141 tggaggagtc caggatagct cttcatgtta ttttcacctt gaggaattgt ccattacatc
1201 tatgagcctt atgtgtggct ttctccgata tagaaaccta tcaggtgtct tttagatcat
1261 ttcaaaacac tggcttattc tttcttatgt ttccaactga agtctgcatc ccaagatgta
1321 gtttcactgc taccccatat ggcacccttg tacgaatttg aaaaaagtac tcactctagg
1381 cacatgcaga gccatgcctg cggggacagc ttagagagta gagggtgggc tgaactccag
1441 ttactctcgt acagggatcc acctttttgc agaaatcaca gtgtggctat ggtgtggttt
1501 gatttcataa aacagatgct taaaagtaa aaaaaaaa
```

Figure 2

```
   1 cttgaatctt ggggcaggaa ctcagaaaac ttccagcccg ggcagcgcgc gcttggtgca
  61 agactcagga gctagcagcc cgtcccctc cgactctccg gtgccgccgc tgcctgctcc
 121 cgccaccta ggaggcgcgg tgccacccac tactctgtcc tctgcctgtg ctccgtgccc
 181 gaccctatcc cggcggagtc tccccatcct cctttgcttt ccgactgccc aaggcacttt
 241 caatctcaat ctcttctctc tctctctctc tctctctctc tctctctctc tctctctctc
 301 tctctctctc gcagggtggg gggaagagga ggaggaattc tttccccgcc taacatttca
 361 agggacacaa ttcactccaa gtctcttccc tttccaagcc gcttccgaag tgctcccggt
 421 gcccgcaact cctgatccca acccgcgaga ggagcctctg cgacctcaaa gcctctcttc
 481 cttctccctc gcttccctcc tcctcttgct acctccacct ccaccgccac ctccacctcc
 541 ggcacccacc caccgccgcc gccgccaccg gcagcgcctc ctcctctcct cctcctcctc
 601 ccctcttctc tttttggcag ccgctggacg tccggtgttg atggtggcag cggcggcagc
 661 ctaagcaaca gcagccctcg cagcccgcca gctcgcgctc gccccgccgg cgtcccagc
 721 cctatcacct catctcccga aaggtgctgg gcagctccgg ggcggtcgag gcgaagcggc
 781 tgcagcggcg gtagcggcgg cgggaggcag gatgagcgca cgcggtgagg gcgcggggca
 841 gccgtccact tcagcccagg gacaacctgc cgccccagcg cctcagaaga gaggacgcgg
 901 ccgccccagg aagcagcagc aagaaccaac cggtgagccc tctcctaaga gacccagggg
 961 aagacccaaa ggcagcaaaa acaagagtcc ctctaaagca gctcaaaaga aagcagaagc
1021 cactggagaa aaacggccaa gaggcagacc taggaaatgg tggttgctaa tgaagagccc
1081 gtgctggtga aggaagcctg ctgatcccgg aactggcctt gcgcgcaagt ggtgggatga
1141 cagacacatt cccttccttg aactgcactc ttttcccttg cactcagagg tggcccgaga
1201 gagccccgcc acaacaagtt gttcagaaga agcctgctca ggaggaaact gaagagacat
1261 cctcacaaga gtctgccgaa gaggactagg gggcgccaac gttcgatttc tacctcagca
1321 gcagttggat cttttgaagg gagaagacac tgcagtgacc acttattctg tattgccatg
1381 gtctttccac tttcatctgg ggtggggtgg ggtggggtgg gggaggggg ggtggggtgg
1441 ggagaaatca cataacctta aaaggacta tattaatcac cttctttgta atcccttcac
1501 agtcccaggt ttagtgaaaa actgctgtaa acacagggga cacagcttaa caatgcaact
1561 tttaattact gttttctttt ttcttaacct actaatagtt tgttgatctg ataagcaaga
1621 gtgggcgggt gagaaaaacc gaattgggtt tagtcaatca ctgcactgca tgcaaacaag
1681 aaacgtgtca cacttgtgac gtcgggcatt catataggaa gaacgcggtg tgtaacactg
1741 tgtacacctc aaataccacc caacccact ccctgtagtg aatcctctgt ttagaacacc
1801 aaagataagg actagatact actttctctt tttcgtataa tcttgtagac acttacttga
1861 tgatttttaa cttttatt ctaaatgaga cgaaatgctg atgtatcctt tcattcagct
1921 aacaaactag aaaaggttat gttcattttt caaaaggga agtaagcaaa caaatattgc
1981 caactcttct atttatggat atcacacata tcagcaggag taataaattt actcacagca
2041 cttgttttca ggacaacact tcattttcag gaaatctact tcctacagag ccaaaatgcc
2101 atttagcaat aaataacact tgtcagcctc agagcattta aggaaactag acaagtaaaa
2161 ttatcctctt tgtaatttaa tgaaaggta caacagaata atgcatgatg aactcaccta
2221 attatgaggt gggaggagcg aaatctaaat ttcttttgct atagttatac atcaatttaa
2281 aaagcaaaaa aaaaaaggg gggggcaatc tctctctgtg tcttttctctc tctctcttcc
2341 tctccctctc tcttttcatt gtgtatcagt ttccatgaaa gacctgaata ccacttacct
2401 caaattaagc atatgtgtta cttcaagtaa tacgttttga cataagatgg ttgaccaagg
2461 tgcttttctt cggcttgagt tcaccatctc ttcattcaaa ctgcactttt agccagagat
2521 gcaatatatc cccactactc aatactacct ctgaatgtta caacgaattt acagtcagt
2581 acttattaca tgctgctata cacaagcaat gcaagaaaaa aacttactgg gtaggtgatt
2641 ctaatcatct gcagttcttt ttgtacactt aattacagtt aaagaagcaa tctccttact
2701 gtgtttcagc atgactatgt attttctat gtttttttaa ttaaaatttt ttaaaatact
2761 tgtttcagct tctctgctag atttctacat taacttgaaa atttttttaac caagtcgctc
2821 ctaggttctt aaggataatt ttcctcaatc acactacaca tcacacaaga tttgactgta
2881 atatttaaat attaccctcc aagtctgtac ctcaaatgaa ttctttaagg agatggacta
2941 attgacttgc aaagacctac ctccagactt caaaaggaat gaacttgtta cttcagcat
3001 tcatttgttt tttcaatgtt tgaaatagtt caaactgcag ctaaccctag tcaaaactat
3061 ttttgtaaaa gacatttgat agaaaggaac acgttttac atacttttgc aaaataagta
3121 aataataaat aaaataaaag ccaaccttca aagaaacttg aagctttgta ggtgagatgc
3181 aacaagccct gcttttgcat aatgcaatca aaaatatgtg ttttaagat tagttgaata
3241 taagaaaatg cttgacaaat attttcatgt attttacaca aatgtgattt ttgtaatatg
```

Figure 3

```
3301 tctcaaccag atttatttta aacgcttctt atgtagagtt tttatgcctt tctctcctag
3361 tgagtgtgct gacttttaa catggtatta tcaactgggc caggaggtag tttctcatga
3421 cggcttttgt cagtatggct tttagtactg aagccaaatg aaactcaaaa ccatctctct
3481 tccagctgct tcagggaggt agtttcaaag gccacatacc tctctgagac tggcagatcg
3541 ctcactgttg tgaatcacca aaggagctat ggagagaatt aaaactcaac attactgtta
3601 actgtgcgtt aaataagcaa ataaacagtg gctcataaaa ataaaagtcg cattccatat
3661 ctttggatgg gcctttaga aacctcattg gccagctcat aaaatggaag caattgctca
3721 tgttggccaa acatggtgca ccgagtgatt tccatctctg gtaaagttac acttttattt
3781 cctgtatgtt gtacaatcaa aacacactac tacctcttaa gtcccagtat acctcatttt
3841 tcatactgaa aaaaaaagct tgtggccaat ggaacagtaa gaacatcata aaattttat
3901 atatatagtt tatttttgtg ggagataaat tttataggac tgttctttgc tgttgttggt
3961 cgcagctaca taagactgga catttaactt ttctaccatt tctgcaagtt aggtatgttt
4021 gcaggagaaa agtatcaaga cgtttaactg cagttgactt tctccctgtt cctttgagtg
4081 tcttctaact ttattctttg ttctttatgt agaattgctg tctatgattg tactttgaat
4141 cgcttgcttg ttgaaaatat ttctctagtg tattatcact gtctgttctg cacaataaac
4201 ataacagcct ctgtgatccc catgtgtttt gattcctgct ctttgttaca gttccattaa
4261 atgagtaata aagtttggtc aaaacagaaa aaaaaaa
```

Figure 3 (cont.)

```
1   msargegagq pstsaqgqpa apapqkrgrg rprkqqqept gepspkrprg rpkgsknksp
61  skaaqkkaea tgekrprgrp rkwpqqvvqk kpaqeeteet ssqesaeed
```

Human HMGA2 Variant 1

---

```
1   msargegagq pstsaqgqpa apapqkrgrg rprkqqqept gepspkrprg rpkgsknksp
61  skaaqkkaea tgekrprgrp rkwdnllprt sskkktslgn stkrsh
```

Human HMGA2 Variant 2

---

```
1   msargegagq pstsaqgqpa apapqkrgrg rprkqqqept gepspkrprg rpkgsknksp
61  skaaqkkaea tgekrprgrp rkwwllmksp cw
```

Human HMGA2 Variant 3

Figure 4

SEQUENCE LISTING

```
<160> NUMBER OF SEQ ID NOS: 12

<210> SEQ ID NO 1
<211> LENGTH: 109
<212> TYPE: PRT
<213> ORGANISM: Homo sapiens

<400> SEQUENCE: 1

Met Ser Ala Arg Gly Glu Gly Ala Gly Gln Pro Ser Thr Ser Ala Gln
1               5                   10                  15

Gly Gln Pro Ala Ala Pro Ala Pro Gln Lys Arg Gly Arg Gly Arg Pro
            20                  25                  30

Arg Lys Gln Gln Gln Glu Pro Thr Gly Glu Pro Ser Pro Lys Arg Pro
        35                  40                  45

Arg Gly Arg Pro Lys Gly Ser Lys Asn Lys Ser Pro Ser Lys Ala Ala
    50                  55                  60

Gln Lys Lys Ala Glu Ala Thr Gly Glu Lys Arg Pro Arg Gly Arg Pro
65                  70                  75                  80

Arg Lys Trp Pro Gln Gln Val Val Gln Lys Lys Pro Ala Gln Glu Glu
                85                  90                  95

Thr Glu Glu Thr Ser Ser Gln Glu Ser Ala Glu Glu Asp
            100                 105

<210> SEQ ID NO 2
<211> LENGTH: 106
<212> TYPE: PRT
<213> ORGANISM: Homo sapiens

<400> SEQUENCE: 2

Met Ser Ala Arg Gly Glu Gly Ala Gly Gln Pro Ser Thr Ser Ala Gln
1               5                   10                  15

Gly Gln Pro Ala Ala Pro Ala Pro Gln Lys Arg Gly Arg Gly Arg Pro
            20                  25                  30

Arg Lys Gln Gln Gln Glu Pro Thr Gly Glu Pro Ser Pro Lys Arg Pro
        35                  40                  45

Arg Gly Arg Pro Lys Gly Ser Lys Asn Lys Ser Pro Ser Lys Ala Ala
    50                  55                  60

Gln Lys Lys Ala Glu Ala Thr Gly Glu Lys Arg Pro Arg Gly Arg Pro
65                  70                  75                  80

Arg Lys Trp Asp Asn Leu Leu Pro Arg Thr Ser Ser Lys Lys Lys Thr
                85                  90                  95

Ser Leu Gly Asn Ser Thr Lys Arg Ser His
            100                 105

<210> SEQ ID NO 3
<211> LENGTH: 92
<212> TYPE: PRT
<213> ORGANISM: Homo sapiens
```

```
<400> SEQUENCE: 3

Met Ser Ala Arg Gly Glu Gly Ala Gly Gln Pro Ser Thr Ser Ala Gln
1               5                   10                  15

Gly Gln Pro Ala Ala Pro Ala Pro Gln Lys Arg Gly Arg Gly Arg Pro
            20                  25                  30

Arg Lys Gln Gln Gln Glu Pro Thr Gly Glu Pro Ser Pro Lys Arg Pro
        35                  40                  45

Arg Gly Arg Pro Lys Gly Ser Lys Asn Lys Ser Pro Ser Lys Ala Ala
    50                  55                  60

Gln Lys Lys Ala Glu Ala Thr Gly Glu Lys Arg Pro Arg Gly Arg Pro
65              70                  75                  80

Arg Lys Trp Trp Leu Leu Met Lys Ser Pro Cys Trp
            85                  90

<210> SEQ ID NO 4
<211> LENGTH: 4150
<212> TYPE: DNA
<213> ORGANISM: Homo sapiens

<400> SEQUENCE: 4
```

| | | | | | |
|---|---|---|---|---|---|
| cttgaatctt | ggggcaggaa | ctcagaaaac | ttccagcccg | gcagcgcgc | gcttggtgca | 60 |
| agactcagga | gctagcagcc | cgtccccctc | cgactctccg | gtgccgccgc | tgcctgctcc | 120 |
| cgccacccta | ggaggcgcgg | tgccacccac | tactctgtcc | tctgcctgtg | ctccgtgccc | 180 |
| gaccctatcc | cggcggagtc | tccccatcct | cctttgcttt | ccgactgccc | aaggcacttt | 240 |
| caatctcaat | ctcttctctc | tctctctctc | tctctctctc | tctctctctc | tctctctctc | 300 |
| tctctctctc | gcagggtggg | gggaagagga | ggaggaattc | tttccccgcc | taacatttca | 360 |
| agggacacaa | ttcactccaa | gtctcttccc | tttccaagcc | gcttccgaag | tgctcccggt | 420 |
| gcccgcaact | cctgatccca | acccgcgaga | ggagcctctg | cgacctcaaa | gcctctcttc | 480 |
| cttctccctc | gcttccctcc | tcctcttgct | acctccacct | ccaccgccac | ctccacctcc | 540 |
| ggcacccacc | caccgccgcc | gccgccaccg | gcagcgcctc | ctcctctcct | cctcctcctc | 600 |
| ccctcttctc | tttttggcag | ccgctggacg | tccggtgttg | atggtggcag | cggcggcagc | 660 |
| ctaagcaaca | gcagccctcg | cagcccgcca | gctcgcgctc | gccccgcgg | cgtccccagc | 720 |
| cctatcacct | catctcccga | aggtgctggg | gcagctccgg | ggcggtcgag | gcgaagcggc | 780 |
| tgcagcggcg | gtagcggcgg | cgggaggcag | gatgagcgca | cgcggtgagg | gcgcggggca | 840 |
| gccgtccact | tcagcccagg | gacaacctgc | cgccccagcg | cctcagaaga | gaggacgcgg | 900 |
| ccgcccagg | aagcagcagc | aagaaccaac | cggtgagccc | tctcctaaga | gacccagggg | 960 |
| aagacccaaa | ggcagcaaaa | acaagagtcc | ctctaaagca | gctcaaaaga | aagcagaagc | 1020 |
| cactggagaa | aaacggccaa | gaggcagacc | taggaaatgg | ccacaacaag | ttgttcagaa | 1080 |
| gaagcctgct | caggaggaaa | ctgaagagac | atcctcacaa | gagtctgccg | aagaggacta | 1140 |
| gggggcgcca | acgttcgatt | tctacctcag | cagcagttgg | atcttttgaa | gggagaagac | 1200 |
| actgcagtga | ccacttattc | tgtattgcca | tggtctttcc | actttcatct | ggggtggggt | 1260 |
| ggggtgggt | gggggagggg | ggggtggggt | gggagaaat | cacataaccct | taaaaggac | 1320 |
| tatattaatc | accttctttg | taatcccttc | acagtcccag | gtttagtgaa | aaactgctgt | 1380 |
| aaacacaggg | gacacagctt | aacaatgcaa | cttttaatta | ctgttttctt | ttttcttaac | 1440 |
| ctactaaatag | tttgttgatc | tgataagcaa | gagtgggcgg | gtgagaaaaa | ccgaattggg | 1500 |
| tttagtcaat | cactgcactg | catgcaaaca | agaaacgtgt | cacacttgtg | acgtcgggca | 1560 |

```
ttcatatagg aagaacgcgg tgtgtaacac tgtgtacacc tcaaatacca ccccaaccca    1620
ctccctgtag tgaatcctct gtttagaaca ccaaagataa ggactagata ctactttctc    1680
tttttcgtat aatcttgtag acacttactt gatgattttt aacttttat ttctaaatga     1740
gacgaaatgc tgatgtatcc tttcattcag ctaacaaact agaaaggtt atgttcattt     1800
ttcaaaaagg gaagtaagca aacaaatatt gccaactctt ctatttatgg atatcacaca    1860
tatcagcagg agtaataaat ttactcacag cacttgtttt caggacaaca cttcattttc    1920
aggaaatcta cttcctacag agccaaaatg ccatttagca ataaataaca cttgtcagcc    1980
tcagagcatt taaggaaact agacaagtaa aattatcctc tttgtaattt aatgaaaagg    2040
tacaacagaa taatgcatga tgaactcacc taattatgag gtgggaggag cgaaatctaa    2100
atttcttttg ctatagttat acatcaattt aaaaagcaaa aaaaaaaag ggggggcaa      2160
tctctctctg tgtctttctc tctctctctt cctctccctc tctcttttca ttgtgtatca    2220
gtttccatga aagacctgaa taccacttac ctcaaattaa gcatatgtgt tacttcaagt    2280
aatacgtttt gacataagat ggttgaccaa ggtgcttttc ttcggcttga gttcaccatc    2340
tcttcattca aactgcactt ttagccagag atgcaatata tccccactac tcaatactac    2400
ctctgaatgt tacaacgaat ttacagtcta gtacttatta catgctgcta tacacaagca    2460
atgcaagaaa aaaacttact gggtaggtga ttctaatcat ctgcagttct ttttgtacac    2520
ttaattacag ttaaagaagc aatctcctta ctgtgtttca gcatgactat gtatttttct    2580
atgttttttt aattaaaaat ttttaaaata cttgtttcag cttctctgct agatttctac    2640
attaacttga aaattttta accaagtcgc tcctaggttc ttaaggataa ttttcctcaa     2700
tcacactaca catcacacaa gatttgactg taatatttaa atattaccct ccaagtctgt    2760
acctcaaatg aattctttaa ggagatggac taattgactt gcaagacct acctccagac     2820
ttcaaaagga atgaacttgt tacttgcagc attcattgt ttttcaatg tttgaaatag      2880
ttcaaactgc agctaaccct agtcaaaact attttgtaa agacatttg atagaaagga      2940
acacgttttt acatactttt gcaaaataag taaataataa ataaaataaa agccaacctt    3000
caaagaaact tgaagctttg taggtgagat gcaacaagcc ctgcttttgc ataatgcaat    3060
caaaaatatg tgttttaag attagttgaa tataagaaaa tgcttgacaa atattttcat    3120
gtattttaca caaatgtgat ttttgtaata tgtctcaacc agatttatt taaacgcttc     3180
ttatgtagag ttttatgcc tttctctcct agtgagtgtg ctgactttt aacatggtat      3240
tatcaactgg gccaggaggt agtttctcat gacggctttt gtcagtatgg cttttagtac    3300
tgaagccaaa tgaaactcaa aaccatctct cttccagctg cttcagggag gtagtttcaa    3360
aggccacata cctctctgag actggcagat cgctcactgt tgtgaatcac caaaggagct    3420
atggagagaa ttaaaactca acattactgt taactgtgcg ttaaataagc aaataaacag    3480
tggctcataa aaataaaagt cgcattccat atctttggat gggccttta gaaacctcat     3540
tggccagctc ataaaatgga agcaattgct catgttggcc aaacatggtg caccgagtga    3600
tttccatctc tggtaaagtt acacttttat ttcctgtatg ttgtacaatc aaaacacact    3660
actacctctt aagtcccagt atacctcatt tttcatactg aaaaaaaaag cttgtggcca    3720
atggaacagt aagaacatca taaaattttt atatatatag tttattttg tgggagataa     3780
atttataggg actgttcttt gctgttgttg gtcgcagcta cataagactg gacatttaac    3840
ttttctacca tttctgcaag ttaggtatgt ttgcaggaga aaagtatcaa gacgtttaac    3900
```

-continued

```
tgcagttgac tttctccctg ttcctttgag tgtcttctaa ctttattctt tgttctttat      3960
gtagaattgc tgtctatgat tgtactttga atcgcttgct tgttgaaaat atttctctag      4020
tgtattatca ctgtctgttc tgcacaataa acataacagc ctctgtgatc cccatgtgtt      4080
ttgattcctg ctctttgtta cagttccatt aaatgagtaa taaagtttgg tcaaaacaga      4140
aaaaaaaaaa                                                             4150
```

<210> SEQ ID NO 5
<211> LENGTH: 1539
<212> TYPE: DNA
<213> ORGANISM: Homo sapiens

<400> SEQUENCE: 5

```
cttgaatctt ggggcaggaa ctcagaaaac ttccagcccg ggcagcgcgc gcttggtgca        60
agactcagga gctagcagcc cgtccccctc cgactctccg gtgccgccgc tgcctgctcc       120
cgccacccta ggaggcgcgg tgccacccac tactctgtcc tctgcctgtg ctccgtgccc       180
gaccctatcc cggcggagtc tccccatcct cctttgcttt ccgactgccc aaggcacttt       240
caatctcaat ctcttctctc tctctctctc tctctctctc tctctctctc tctctctctc       300
tctctctctc gcagggtggg gggaagagga ggaggaattc tttccccgcc taacatttca       360
agggacacaa ttcactccaa gtctcttccc tttccaagcc gcttccgaag tgctcccggt       420
gcccgcaact cctgatccca cccgcgaga ggagcctctg cgacctcaaa gcctctcttc        480
cttctccctc gcttccctcc tctcttgct acctccacct ccaccgccac ctccacctcc        540
ggcacccacc caccgccgcc gccgccaccg gcagcgcctc ctcctctcct cctcctcctc       600
ccctcttctc tttttggcag ccgctggacg tccggtgttg atggtggcag cggcggcagc       660
ctaagcaaca gcagccctcg cagcccgcca gctcgcgctc gccccgccgg cgtccccagc       720
cctatcacct catctcccga aaggtgctgg gcagctccgg ggcggtcgag gcgaagcggc       780
tgcagcggcg gtagcggcgg cgggaggcag gatgagcgca cgcggtgagg gcgcggggca       840
gccgtccact tcagcccagg gacaacctgc cgccccagcg cctcagaaga gaggacgcgg       900 ccgcccagg aagcagcagc aagaaccaac cggtgagccc tctcctaaga gacccagggg        960
aagacccaaa ggcagcaaaa acaagagtcc ctctaaagca gctcaaaaga aagcagaagc      1020
cactggagaa aaacggccaa gaggcagacc taggaaatgg gacaatctac taccaagaac     1080
cagctccaag aagaaaacat ctctgggaaa cagtaccaaa aggagtcact gaattgtcat     1140
tggaggagtc caggatagct cttcatgtta ttttcacctt gaggaattgt ccattacatc     1200
tatgagcctt atgtgtggct ttctccgata tagaaaccta tcaggtgtct tttagatcat     1260
ttcaaaacac tggcttattc tttcttatgt ttccaactga agtctgcatc ccaagatgta     1320
gtttcactgc taccccatat ggcacccttg tacgaatttg aaaaaagtac tcactctagg      1380
cacatgcaga gccatgcctg cggggacagc ttagagagta gaggtgggc tgaactccag      1440 ttactctcgt acagggatcc accttttgc agaaatcaca gtgtggctat ggtgtggttt      1500
gatttcataa aacagatgct taaaaagtaa aaaaaaaa                              1539
```

<210> SEQ ID NO 6
<211> LENGTH: 4298
<212> TYPE: DNA
<213> ORGANISM: Homo sapiens

<400> SEQUENCE: 6

```
cttgaatctt ggggcaggaa ctcagaaaac ttccagcccg ggcagcgcgc gcttggtgca        60
```

```
agactcagga gctagcagcc cgtcccsctc cgactctccg gtgccgccgc tgcctgctcc    120
cgccacccta ggaggcgcgg tgccacccac tactctgtcc tctgcctgtg ctccgtgccc    180
gaccctatcc cggcggagtc tccccatcct cctttgcttt ccgactgccc aaggcacttt    240
caatctcaat ctcttctctc tctctctctc tctctctctc tctctctctc tctctctctc    300
tctctctctc gcagggtggg gggaagagga ggaggaattc tttccccgcc taacatttca    360
agggacacaa ttcactccaa gtctcttccc tttccaagcc gcttccgaag tgctcccggt    420
gcccgcaact cctgatccca acccgcgaga ggagcctctg cgacctcaaa gcctctcttc    480
cttctccctc gcttccctcc tcctcttgct acctccacct ccaccgccac ctccacctcc    540
ggcacccacc caccgccgcc gccgccaccg gcagcgcctc ctcctctcct cctcctcctc    600
ccctcttctc ttttttggcag ccgctggacg tccggtgttg atggtggcag cggcggcagc   660
ctaagcaaca gcagccctcg cagcccgcca gctcgcgctc gccccgccgg cgtcccacgc   720
cctatcacct catctcccga aggtgctggg gcagctccgg ggcggtcgag gcgaagcggc    780
tgcagcggcg gtagcggcgg cgggaggcag gatgagcgca cgcggtgagg gcgcggggca    840
gccgtccact tcagcccagg gacaacctgc cgccccagcg cctcagaaga gaggacgcgg    900
ccgccccagg aagcagcagc aagaaccaac cggtgagccc tctcctaaga gacccagggg    960
aagacccaaa ggcagcaaaa acaagagtcc ctctaaagca gctcaaaaga aagcagaagc   1020
cactggagaa aaacggccaa gaggcagacc taggaaatgg tggttgctaa tgaagagccc   1080
gtgctggtga aggaagcctg ctgatcccgg aactggcctt gcgcgcaagt ggtgggatga   1140
cagacacatt cccttccttg aactgcactc ttttccctttg cactcagagg tggcccgaga   1200
gagccccgcc acaacaagtt gttcagaaga agcctgctca ggaggaaact gaagagacat   1260
cctcacaaga gtctgccgaa gaggactagg gggcgccaac gttcgatttc tacctcagca   1320
gcagttggat cttttgaagg gagaagacac tgcagtgacc acttattctg tattgccatg   1380
gtctttccac tttcatctgg ggtgggggtgg ggtggggtgg gggaggggggg ggtggggtgg   1440
ggagaaatca cataacctta aaaggacta tattaatcac cttctttgta atcccttcac    1500
agtcccaggt ttagtgaaaa actgctgtaa acacagggga cacagcttaa caatgcaact   1560
tttaattact gttttctttt tcttaacct actaatagtt tgttgatctg ataagcaaga    1620
gtgggcgggt gagaaaaacc gaattgggtt tagtcaatca ctgcactgca tgcaaacaag   1680
aaacgtgtca cacttgtgac gtcgggcatt catataggaa gaacgcggtg tgtaacactg    1740
tgtacacctc aaataccacc ccaacccact ccctgtagtg aatcctctgt ttagaacacc    1800
aaagataagg actagatact actttctctt tttcgtataa tcttgtagac acttacttga    1860
tgatttttaa cttttatt ctaaatgaga cgaaatgctg atgtatcctt tcattcagct     1920
aacaaactag aaaaggttat gttcattttt caaaaggga agtaagcaaa caaatattgc    1980
caactcttct atttatggat atcacacata tcagcaggag taataaattt actcacagca   2040
cttgttttca ggacaacact tcattttcag gaaatctact tcctacagag ccaaaatgcc   2100
atttagcaat aaataacact tgtcagcctc agagcattta aggaaactag acaagtaaaa   2160
ttatcctctt tgtaatttaa tgaaaaggta caacagaata atgcatgatg aactcaccta   2220
attatgaggt gggaggagcg aaatctaaat ttcttttgct atagttatac atcaatttaa   2280
aaagcaaaaa aaaaaagggg gggggcaatc tctctctgtg tctttctctc tctctcttcc   2340
tctccctctc tcttttcatt gtgtatcagt ttccatgaaa gacctgaata ccacttacct   2400
```

-continued

```
caaattaagc atatgtgtta cttcaagtaa tacgttttga cataagatgg ttgaccaagg    2460
tgctttcctt cggcttgagt tcaccatctc ttcattcaaa ctgcacttt agccagagat     2520 gcaatatatc cccactactc aatactacct ctgaatgtta caacgaattt acagtctagt    2580
acttattaca tgctgctata cacaagcaat gcaagaaaaa aacttactgg gtaggtgatt    2640
ctaatcatct gcagttcttt ttgtacactt aattacagtt aaagaagcaa tctccttact    2700
gtgtttcagc atgactatgt attttctat gttttttaa ttaaaattt ttaaaatact       2760 tgtttcagct tctctgctag atttctacat taacttgaaa attttttaac caagtcgctc    2820
ctaggttctt aaggataatt ttcctcaatc acactcacaa tcacacaaga tttgactgta    2880
atatttaaat attaccctcc aagtctgtac ctcaaatgaa ttctttaagg agatggacta    2940
attgacttgc aaagacctac ctccagactt caaaaggaat gaacttgtta cttgcagcat    3000
tcatttgttt tttcaatgtt tgaaatagtt caaactgcag ctaaccctag tcaaaactat    3060
ttttgtaaaa gacatttgat agaaaggaac acgtttttac atactttgc aaaataagta     3120 aataataaat aaaataaaag ccaaccttca aagaaacttg aagctttgta ggtgagatgc    3180
aacaagccct gcttttgcat aatgcaatca aaaatatgtg ttttaagat tagttgaata    3240 taagaaaatg cttgacaaat attttcatgt attttacaca aatgtgattt ttgtaatatg    3300
tctcaaccag atttattta aacgcttctt atgtagagtt tttatgcctt tctctcctag     3360
tgagtgtgct gactttttaa catggtatta tcaactgggc caggaggtag tttctcatga    3420
cggcttttgt cagtatggct tttagtactg aagccaaatg aaactcaaaa ccatctctct    3480
tccagctgct tcagggaggt agtttcaaag gccacatacc tctctgagac tggcagatcg    3540
ctcactgttg tgaatcacca aaggagctat ggagagaatt aaaactcaac attactgtta    3600
actgtgcgtt aaataagcaa ataaacagtg gctcataaaa ataaaagtcg cattccatat    3660
ctttggatgg gccttttaga aacctcattg gccagctcat aaaatggaag caattgctca    3720
tgttggccaa acatggtgca ccgagtgatt tccatctctg gtaaagttac acttttattt    3780
cctgtatgtt gtacaatcaa aacacactac tacctcttaa gtcccagtat acctcatttt    3840
tcatactgaa aaaaaaagct tgtggccaat ggaacagtaa gaacatcata aaattttat     3900 atatatagtt tatttttgtg ggagataaat tttataggac tgttctttgc tgttgttggt    3960
cgcagctaca taagactgga catttaactt ttctaccatt tctgcaagtt aggtatgttt    4020
gcaggagaaa agtatcaaga cgtttaactg cagttgactt tctccctgtt cctttgagtg    4080
tcttctaact ttattctttg ttctttatgt agaattgctg tctatgattg tactttgaat    4140
cgcttgcttg ttgaaaatat ttctctagtg tattatcact gtctgttctg cacaataaac    4200
ataacagcct ctgtgatccc catgtgtttt gattcctgct ctttgttaca gttccattaa    4260
atgagtaata aagtttggtc aaaacagaaa aaaaaaa                             4298
```

<210> SEQ ID NO 7
<211> LENGTH: 2701
<212> TYPE: DNA
<213> ORGANISM: Homo sapiens
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature

```
<222> LOCATION: (386)..(386)
<223> OTHER INFORMATION: n is a, c, g, or t
<220> FEATURE:
<221> NAME/KEY: misc_feature
<222> LOCATION: (2432)..(2437)
<223> OTHER INFORMATION: n is a, c, g, or t
<220> FEATURE:
<221> NAME/KEY: misc_feature
<222> LOCATION: (2482)..(2482)
<223> OTHER INFORMATION: n is a, c, g, or t
<220> FEATURE:
<221> NAME/KEY: misc_feature
<222> LOCATION: (2493)..(2493)
<223> OTHER INFORMATION: n is a, c, g, or t
<220> FEATURE:
<221> NAME/KEY: misc_feature
<222> LOCATION: (2495)..(2495)
<223> OTHER INFORMATION: n is a, c, g, or t
<220> FEATURE:
<221> NAME/KEY: misc_feature
<222> LOCATION: (2501)..(2501)
<223> OTHER INFORMATION: n is a, c, g, or t
<220> FEATURE:
<221> NAME/KEY: misc_feature
<222> LOCATION: (2550)..(2550)
<223> OTHER INFORMATION: n is a, c, g, or t
<220> FEATURE:
<221> NAME/KEY: misc_feature
<222> LOCATION: (2564)..(2564)
<223> OTHER INFORMATION: n is a, c, g, or t
<220> FEATURE:
<221> NAME/KEY: misc_feature
<222> LOCATION: (2603)..(2603)
<223> OTHER INFORMATION: n is a, c, g, or t
<220> FEATURE:
<221> NAME/KEY: misc_feature
<222> LOCATION: (2670)..(2670)
<223> OTHER INFORMATION: n is a, c, g, or t

<400> SEQUENCE: 7
ctgcagagca ctcaacgtgc agcaaagtgt cccagctctg caaagggcag ctggaaatgg      60
atttaaaatg gcaacgcgga ccaatcagcg ctgccgcnca aaagcagaca tttacacgcg     120
cctcctccac atgcacagcg gaacctngcg gtgcctaact cctgcttagg gctgcaaagt     180
aggcgttttt attccacggt ggtctgtatc tttgaaaaaa ataaattctt ccccaggtga     240 aagttttat tttggaatta gtccaaaata attttgggtg tgatgtgtga aaatctgaac     300
ctaatttttt cagagttttg tgttattcaa ggatgaaaag aggtacattt aaaaatgtac     360 tccaccttt aaaaacggac tgtggncatt atggtgttca cataactcag aacagcccag     420
gccataaaat taggacttgg cagaaagaga gttctcaggc agaaggttaa atcgaggtaa     480
actgaaggga gagttgggca gtgagtgcaa ttgtggtgtt aggaatctac aaggtgccct     540
ttaccctggg aacatcggat tcccggggag ggggatgggg agggaacttc ggttgcctct     600 agtcttttcct ggagaaaaaa gttcaatgaa gaagctgggg cgctctgtgt gtgcacattg     660
tttgcatgtg tctgcgaatg tgcatgtcta tctgcgtgcc tgtgtgtatg tgtgtgtgtg     720
taaatgcggg tgtttaccag cgcatgaatg ccccccgtgt ccacgtgtat ctgcgtgcat     780
gtgcttacac gcgtgttcgt gtgtatctgc atgcatgtct ccgtgtatgt gcgcgctcgc     840
ccgcgcgcag gctctgtggt gagggcattc cgaggcggag tacggctgtc aggggacctc     900
tcccactcca ctgcagtccc ttcccactca cagtgaaccg gtgcgctgcc tgaggtgcag     960
cctagacgct tcctgcaaag tgttggctcg gcacggtaga ggcgcaggta aaggccaagc    1020
cccgaaacgt ggctccggga cagtcacgtt cccgcgcctt cccaggacaa ctgcccaggg    1080
gtgacctcga gaggcgggtg gagctaggcc cacggcgagc cagcccggga tcccggcctg    1140
```

-continued

```
tcctttaacc cgccgccggg cgggagcacg tgagcgggc tccgggtggc acccgggcgc    1200
cgccgccgcc gaggcagttg tatttcgaac gctgcctctg ctagcagcc aggcgccttg    1260
gctcggcggt ccgcctggcc tccctcctcc tcatactttt cttcctgcgc aaccccctcc    1320
cctttatccg cccacgatta gaggtgggca ctccccccac caccacccccc tcccaagcg    1380
caagcgcgtg cacgcacaca caccacacac actcacactc acacacactc acacacactc    1440
atcccacttg aatcttgggg caggaactca gaaaacttcc agcccgggca gcgcgcgctt    1500
ggtgcaagac tcaggagcta gcagcccgtc cccctccgac tctccggtgc cgccgctgcc    1560
tgctcccgcc accctaggag gcgcggtgcc acccactact ctgtcctctg cctgtgctcc    1620
gtgcccgacc ctatcccggc ggagtctccc catcctcctt tgctttccga ctgcccaagg    1680
cactttcaat ctcaatctct tctctctctc tctctctctc tctgtctctc tctctctctc    1740
tctctctctc tctctcgcag ggtggggga agaggaggag gaattctttc cccgcctaac    1800
atttcaaggg acacaattca ctccaagtct cttcccttc caagccgctt ccgaagtgct    1860
cccggtgccc gcaactcctg atcccaaccc gcgagaggag cctctgcgac ctcaaagcct    1920
ctcttccttc tccctcgctt ccctcctcct cttgctacct ccacctccac cgccacctcc    1980
acctccggca cccacccacc gccgccgccg ccaccggcag cgcctcctcc tctcctcctc    2040
ctcctccccct cttctctttt tggcagccgc tggacgtccg gtgttgatgg tggcagcggc    2100
ggcagcctaa gcaacagcag ccctcgcagc ccgccagctc gcgctcgccc gccggcgtc    2160
cccagcccta tcacctcatc tcccgaaagg tgctgggcag ctccggggcg gtcgaggcga    2220
agcggctgca gcggcggtag cggcggcggg aggcaggatg agcgcacgcg gtgagggcgc    2280
ggggcagccg tccacttcag cccagggaca acctgccgcc ccagcgcctc agaagagagg    2340
acgcggccgc cccaggaagc agcagcaagt cagtacgagg gcgcggtggg ggcaccagcc    2400
caccccgtcc ccactgccgg ggcccagaca cnnnnnnggc ggccggagtg cgggagccca    2460
gtcgccgcgg ccgtcgcaca cngcccgccg gcngnccggg ngggagcggc gcagacccca    2520
cgagtgcgcc gcgcggcccc ggggcgccan caaccctccg ggcngggagg tggggagccg    2580
cggcgggcgg cccggggaag gcnggaggtg gggtcgggcg aagcgcgtcc tcggactttc    2640
gctattgtgc acggccccga gtggcgcggn gtcgcccagt gactggaagc gaccgggatc    2700
c                                                                   2701
```

<210> SEQ ID NO 8
<211> LENGTH: 108
<212> TYPE: PRT
<213> ORGANISM: Mus musculus

<400> SEQUENCE: 8

```
Met Ser Ala Arg Gly Glu Gly Ala Gly Gln Pro Ser Thr Ser Ala Gln
1               5                   10                  15

Gly Gln Pro Ala Ala Pro Val Pro Gln Lys Arg Gly Arg Gly Arg Pro
            20                  25                  30

Arg Lys Gln Gln Gln Glu Pro Thr Cys Glu Pro Ser Pro Lys Arg Pro
        35                  40                  45

Arg Gly Arg Pro Lys Gly Ser Lys Asn Lys Ser Pro Ser Lys Ala Ala
    50                  55                  60

Gln Lys Lys Ala Glu Thr Ile Gly Glu Lys Arg Pro Arg Gly Arg Pro
65                  70                  75                  80

Arg Lys Trp Pro Gln Gln Val Val Gln Lys Pro Ala Gln Glu Thr
                85                  90                  95
```

Glu Glu Thr Ser Ser Gln Glu Ser Ala Glu Glu Asp
            100                 105

<210> SEQ ID NO 9
<211> LENGTH: 1748
<212> TYPE: DNA
<213> ORGANISM: Mus musculus

<400> SEQUENCE: 9

| | | | | | |
|---|---|---|---|---|---|
| gtgctgggcg | gattcggggc | ggcggaggcc | gagcggctgc | agcggcggta | ccggtagagg | 60 |
| cagtggtagc | ggcggcggga | ggcaggatga | gcgcacgcgg | tgagggcgcc | gggcagccgt | 120 |
| ccacatcagc | ccagggacaa | cctgccgccc | cggtgccaca | gaagcgagga | cgcggccgac | 180 |
| ccaggaagca | gcagcaagag | ccaacctgtg | agccctctcc | taagagaccc | agaggaagac | 240 |
| ccaaaggcag | caaaaacaag | agcccctcta | aagcagccca | gaagaaagca | gagaccattg | 300 |
| gagaaaaacg | gccaagaggc | agacctagga | aatggccaca | caagtcgtt | cagaagaagc | 360 |
| ctgctcagga | gactgaagag | acatcctcgc | aagagtccgc | agaggaggat | taggggcgc | 420 |
| cgacattcaa | tttctacctc | agcatcagtt | ggatctttg | aagggagaag | acactgcagt | 480 |
| gaccagttat | tcttaactgc | cacggtcttt | ctacttcctg | cggggtgggg | cggggcggg | 540 |
| gctgggcgag | gggcggggcc | gggtgggcg | aaatcgcata | accttgagaa | ggactatatt | 600 |
| aatcactttg | taatcccttc | acagtcccag | gtttagtgaa | aaactgctgt | aaacacgggg | 660 |
| gacacagttt | aacaatgcaa | cttttaatga | ctgttttctt | tttccttaac | ttactaatag | 720 |
| tttgtggatc | tgataagcaa | gggtgtgtgg | ttgaagaaaa | cctctgtggt | gggcttaatc | 780 |
| agtcactaca | tgcaaacccct | aaaccggcac | cctggtgacc | gggggcattc | gtataagaaa | 840 |
| agcattgtgt | gtgactctgt | gtccactcag | atgccacccc | caccatgatc | atagaaaatc | 900 |
| tgcttaggac | accaaagatg | agaactagac | actactctcc | tttctttgtg | tataatcttg | 960 |
| tagacactta | cttgattttt | ttttcttttt | ttacttttca | attctgaatg | agacaaaatg | 1020 |
| ctggtgtatc | ttttcataca | gctagcaaac | cagaataggt | tatgctcgtt | ttttgctttg | 1080 |
| ttttgttttt | caaaaaggga | agtaaacgag | aaccgttgac | tcctccatttt | atggactcat | 1140 |
| acacagcagc | aggagtgata | agcccacaag | ctctctttcc | cgcctcggga | aatctacaca | 1200 |
| gccaaaagcc | acttagccat | aaatgacact | tgtcagcctt | gaagcatcgg | agataactag | 1260 |
| ctgagtaaaa | tgatcctgtt | ttggaattta | atgaaaaggt | taacagtacc | caatgaaccc | 1320 |
| acccaagtga | tgacatggga | ggagcgaaac | cgaaatctct | tttgctatat | aaaggacact | 1380 |
| atttttaaa | aaaaaataat | aaaaacagct | cccgctctct | gtcctctctc | cctcccttct | 1440 |
| ctccctcgcc | tctctctcct | ctctatattc | cctgttcttc | attgtgtacc | agtgtccgtg | 1500 |
| aaagaccgca | gtaccactta | cctcagatga | agcctgcgtg | ttacatcctg | taacacctttt | 1560 |
| catttttgaca | taagatggct | agccgaggtg | cattatcttg | gttcggactg | ccatctctgc | 1620 |
| attcacgctg | cacttttagc | cagagatgca | ataatcccca | ctcctcaata | ctacctctga | 1680 |
| atgctacagt | gaatttacag | ccctgcactt | gttacacgct | gctagacaca | agccctgcaa | 1740 |
| aaaaaaaa | | | | | | 1748 |

<210> SEQ ID NO 10
<211> LENGTH: 1047
<212> TYPE: DNA
<213> ORGANISM: Mus musculus

<400> SEQUENCE: 10

-continued

```
cacactcatc cctcttgaat cccgggcagg aactctgaaa acttgcagca cgggcaaaac        60
ttgggctccg ggtgcagagc gcagaggcca gcagcttgtc cctctgcatc tgtgcagtgc       120
cgccgcctga ccccgccacc cgaggaggcg cggtgccacc cactgctctg ttccttgcta       180
gagctgagct gggcgcctac ggatcctggc agaaacttcc actctctcct cggtttctga       240
ccgcactagt cagtctctat ctctgtcccg ttctgtctct ttgtctctgt ctctctctga       300
gtttctgtct ctgtccctct tctctgtgtc tctctctggc tctctgcgtc tctgtctctc       360
cttcccgccc ccctccctct ctctccctct ggggtggggg agaggaggcg gaattctttc       420
cccgcctaac atttcaaggg acacaattca ctccaagtct cttccctctc caagccgctg       480
ccgagcgtcc cagtacccgc aactcccgag cctttgcgag agagcaaccc tctccgcctc       540
caactcttcc ctctccttcg cttcccgcct cctctcccta cctccacctc tacctccgcc       600
acccactgcc cgcagcgcct cctccttcct ctctcctcct ctcctcctcc tctcttcctc       660 ctccoctctc tcttttggc agccgctgac gtccggtgtt gatggtggca gcggcggcag       720
cctaagcagc agcagtagtc cccgcgcact cgccagctcg cctcgtctcg ccgctcttgc       780
cctctccagc tctctacatc ccgtctcccg aaaggtgctg ggcggattcg gggcggcgga       840
ggccgagcgg ctgcagcggc ggtaccggta gaggcagtgg tagcggcggc gggaggcagg       900
atgagcgcac gcggtgaggg cgccgggcag ccgtccacat cagcccaggg acaacctgcc       960
gccccggtgc cacagaagcg aggacgcggc cgacccagga agcagcagca agtcagtacg      1020
ccgacgggag gggccactca gcccacc                                          1047
```

<210> SEQ ID NO 11
<211> LENGTH: 20
<212> TYPE: DNA
<213> ORGANISM: Homo sapiens

<400> SEQUENCE: 11
ccgactgccc aaggcacttt                                                    20

<210> SEQ ID NO 12
<211> LENGTH: 18
<212> TYPE: DNA
<213> ORGANISM: Homo sapiens

<400> SEQUENCE: 12
tcgcgggttg ggatcagg                                                      18

ALLELIC FORM OF THE HMGA2 GENE PREDISPOSING WOMEN TO THE FORMATION OF LEIOMYOMAS

CROSS REFERENCE TO RELATED APPLICATIONS

The present application claims priority to, and the benefit of, U.S. provisional application 60/736,833, filed on Nov. 16, 2005, the contents of which is hereby incorporated by reference in its entirety.

STATEMENT OF GOVERNMENT FUNDING

The United States Government has a paid-up license in this invention and the right in limited circumstances to require the patent owners to license others under reasonable terms as provided for by the terms of NIH Grant No. R01 HD046226, awarded by the Department of Health and Human Services.

FIELD OF THE INVENTION

The present invention is directed to a diagnostic test for determining if a woman carries an allelic form of the HMGA2 gene that predisposes her to the formation of uterine fibroids. This test will be especially useful in women with a family history of fibroid problems and will help both in counseling women with respect to reproductive matters and in helping physicians to select an appropriate therapeutic option. The invention also includes vectors that contain the fibroid-associated allele and cells transformed with these vectors. In addition, the invention includes transgenic mice that have at least one fibroid associated allele and the use of these mice to assay compounds for their potential benefit in treating leiomyomas.

BACKGROUND OF THE INVENTION

Fibroids are benign uterine tumors that have been estimated to occur to some degree in more than 75% of women of reproductive age (*Cancer Research* 62:3766-3772 (2002); Cramer, et al., *Am. J. Clin. Pathol.* 94:435-438 (1990)). About 20-50% of women with fibroids experience symptoms and, depending upon the size and location of their tumors, these may include infertility, urinary incontinence, constipation, menorrhagia (prolonged and profuse uterine bleeding) and abdominal pain (Vollenhoven et al. *Brit. J Obstet. Gynaecol.* 97:285-298 (1990)). More than 200,000 of these women undergo hysterectomies each year in the United States (Walker, et al., *Science* 308:1589-1592 (2005)).

Although the causes of fibroids are not completely understood, genetic factors appear to be an important contributing component. In this regard, recurring cytogenetic abnormalities associated with human leiomyoma have been mapped to two specific high mobility group (HMG) gene loci. Rearrangements at 12q14-15 map to HMGA2, formerly HMGIC, and rearrangements at 6p21 map to HMGA1, formerly HMGI/Y (Hess, et al., *Am. J. Clin. Pathol.* 109:251-261 (1998); Ligon, et al., *Genes Chromosomes Cancer* 28:235-245, (2000)). Alterations involving at least one of these loci have been observed in up to 30% of chromosomally abnormal leiomyomas.

The genetic rearrangements described above are somatic in nature, i.e., they occur in tumor cells and would not ordinarily be expected to be present in the normal cells of a patient or transmitted to a patient's offspring. Whether there are hereditary factors that predispose women to develop these rearrangements or uterine fibroids in general is largely unknown. The identification of such factors could help in counseling women concerning reproductive issues and in deciding between therapeutic options.

SUMMARY OF THE INVENTION

The present invention is directed to a specific allelic form of the HMGA2 gene characterized by 27 repeats of TC in the 5' untranslated region that has been found to be associated with a predisposition for the development of leiomyomas and which is transmitted to offspring. Based upon this finding, a diagnostic test may be performed to identify women that carry the fibroid associated allele and who, as a result, are at greatly increased risk of having problems with fibroid tumors. Such women may be more closely monitored and, since they are more likely to experience recurring, symptomatic tumors, may be treated more aggressively.

Human HMGA2 has thus far been found to occur in three variant forms designated herein as variant 1 (also known in the art as "isoform a"), variant 2 (also known in the art as "isoform b") and variant 3 (also known in the art as "isoform c"). DNA sequences for these isoforms are shown in FIGS. 1-3 respectively and a comparison of the variant proteins is shown in FIG. 4. Although the variant forms differ somewhat with respect to the protein that they produce, they are all essentially the same with respect to the portions of their 5' untranslated region (UTR) that are relevant to the present invention. In each case there is a stretch of consecutive TC dinucleotides that are found approximately 550 nucleotides 5' to the ATG start site. The sequence in this section has been found to vary; there may be anywhere between 18 and 37 sequential TCs, each specific length corresponding to a different HMGA2 allele of either variant 1, 2 or 3. The particular allele that the inventors have found to be associated with a predisposition for uterine fibroid formation occurs when there are 27 consecutive TC repeats. To simplify the description for the purposes of the present invention and because of the great similarity of variants in the region of interest, we will refer simply to an "HMGA2 allele" but, unless otherwise indicated, it will be understood that this term actually refers to any HMGA2 gene having a 5' UTR with the 27 TC repeat element regardless of the HMGA2 variant that this UTR is associated with.

In its first aspect, the invention is directed to a method of assessing the risk of a woman forming uterine fibroids by determining if her genome includes an allelic form of HMGA2 in which the TC dinucleotide is sequentially repeated 27 times in the gene's 5' UTR. Since a genetic predisposition will be present throughout life, women carrying the 27 TC repeat are expected to have recurrent problems and, overall, to be more likely to experience symptomatic fibroids than women that do not have this allele. The number of repeats present may be assessed by PCR amplifying the TC rich portion of the HMGA2 UTR, i.e., by amplifying a sequence lying 400-800 nucleotides 5' (and preferably 500-700 nucleotides 5') to the HMGA2 ATG translation start sequence. The amplification product produced should generally be 54-400 nucleotides in length and may be further characterized by sequence analysis, by size analysis (e.g., using electrophoresis) or by performing a hybridization procedure. Two particular DNA sequences that have been found to be effective as PCR primers for carrying out this analysis (SEQ ID NO:11 and SEQ ID NO:12) are shown in FIGS. 1-3. These primers, or others, may be included as part of a diagnostic kit along with instructions for carrying out the diagnostic assay.

In another aspect, the invention is directed to a substantially pure DNA sequence comprising a region encoding either the human HMGA2 protein variant 1 (SEQ ID NO:1), variant 2 (SEQ ID NO:2) or variant 3 (SEQ ID NO3) or the mouse HMGA2 protein (SEQ ID NO:8). This DNA should also include a 5' UTR having 27 sequential copies of a TC repeat which are preferably located approximately 550 nucleotides 5' to the ATG initiation sequence. The invention also includes vectors containing this DNA and host cells transformed with these vectors.

The invention also encompasses transgenic mice that have been engineered to include an HMGA2 gene with characteristics found to predispose women to the formation of uterine fibroids. Specifically, the gene should have 27 sequentially repeated TC dinucleotides, preferably located 500-700 nucleotides 5' to the ATG translation start codon. The transgenic mice may be used as part of a method for assaying test compounds to determine whether they may be of value in the treatment or prevention of leiomyomas. For example, a test compound may be administered to transgenic mice and then the number and size of uterine fibroid tumors that develop can be determined. By comparing these results with those obtained from similar mice not administered test compound, a conclusion can be reached as to whether the compound is having an effect on the occurrence or severity of fibroid tumor formation.

BRIEF DESCRIPTION OF THE DRAWINGS

FIG. 1: FIG. 1 shows the cDNA sequence of human HMGA2 variant 1 (SEO ID NO:4), including 811 nucleotides in the 5' untranslated region. The TC rich region in the UTR is underlined and two primer sequences successfully used for PCR amplification are shaded. The ATG start site is both underlined and shaded.

FIG. 2: FIG. 2 shows the cDNA sequence of human HMGA2 variant 2 SEO ID NO:5), and also includes 811 nucleotides in the 5' UTR. The TC rich region is underlined and two primer sequences used for PCR amplification are shaded. The ATG start site is both underlined and shaded.

FIG. 3: FIG. 3 shows the cDNA sequence of human HMGA2 variant 3 SEO ID NO:6'). Shading and underlining are the same as for FIGS. 1 and 2. Although the protein encoded by this variant is different than for variants 1 and 2, the location of the ATG start sequence and TC rich region in the UTR is the same. It should also be noted that the same primers can be used for PCR amplification of the TC rich region.

FIG. 4: FIG. 4 shows a comparison of the proteins produced by the three variant HMGA2 DNA sequences (SEO ID NOs: 1 -3'). The portions of the proteins that differ from one another are underlined.

DESCRIPTION OF SEQUENCES

Sequences used herein include HMGA2 protein and nucleotide sequences from both the human and mouse. These sequences are referred to by sequence identification numbers and are shown in the attached sequence listing. They have been described in various references including: Manfioletti, et al., *Nucl. Ac. Res.* 19:6793-6797 (1991); Schoenmakers, et al., *Genes Chromosomes Cancer* 11:106-118 (1994); Zhou, et al., *Nucl. Ac. Res.* 24:4071-4077 (1996); Reeves, et al., *Biochim. Biophys. Acta* 1519:13-29 (2001); Borrmann, et al., *Oncogene* 22:756-760 (2003); and Hauke, et al., *Biochim. Biophys. Acta* 1729:24-31 (2005)). Each sequence is briefly described below;

SEQ ID NO:1 Human HMGA2 variant-1 protein sequence; GenBank accession no. U28749; 109 amino acids long.

SEQ ID NO:2 Human HMGA2 variant-2 protein sequence; NCBI accession no. NP 003475 (GenPrt); 106 amino acids long.

SEQ ID NO:3 Human HMGA2 variant-3 protein sequence; 92 amino acids long; This protein is shorter than either variant 1 or 2 and has a distinct C-terminus.

SEQ ID NO:4 Human HMGA2 variant 1 cDNA sequence including 811 nucleotides in the 5' untranslated region (UTR); GenBank accession no. U28749; ATG initiation codon starts at position 812; TC rich region at positions 255-310.

SEQ ID NO:5 Human HMGA2 variant 2 cDNA sequence including 811 nucleotides in the 5' UTR; coding sequence 812-1141; TC rich region at positions 255-310. This variant has multiple differences in the coding region compared to variant 1, including an alternate exon which results in an early stop codon. The resulting protein has a distinct C-terminus and is shorter than variant 1.

SEQ ID NO:6 Human HMGA2 variant 3 cDNA sequence including 811 nucleotides in the 5' UTR; TC rich region at positions 255-310; coding sequence 812-1090; This variant produces a protein that is shorter than that produced by either variant 1 or 2 but note that the ATG start site and TC rich region are in the same positions.

SEQ ID NO:7 Human genomic sequence of HMGA2 exon 1, including 2257 nucleotides 5' to ATG initiation site (at position 2258); GenBank accession no. U28750; TC rich region found at nucleotides 1701-1754.

SEQ ID NO:8 Mouse HMGA2 protein sequence; NCBI accession no. P52927 (Swissprot); 108 amino acids long.

SEQ ID NO:9 Mouse HMGA2 cDNA sequence including 86 nucleotides in the 5' UTR; GenBank accession no. X58380; ATG initiation codon starts at position 87.

SEQ ID NO:10 Mouse genomic sequence of HMGA2 exon 1, including 900 nucleotides of 5' UTR; GenBank accession no. X99915; ATG initiation codon starts at position 901.

SEQ ID NO:11 First primer for PCR amplification of human HMGA2 sequences.

SEQ ID NO:12 Second primer for PCR amplification of human HMGA2 sequences.

Definitions

The following definitions are provided for the purpose of comprehension of the present invention but are not meant to be limiting.

TC repeats: The present document refers to TC repeat sequences in the 5' UTR of the HMGA2 gene. It will be understood that this means sequential repeats, i.e., 27 TCs in a row, and not repeats located anywhere in the region.

Recurrent fibroids: The term "recurrent fibroids" refers to any new uterine fibroids that recur in the same individual. For example, a woman that has fibroids which, either naturally or as the result of treatment, are eliminated would be said to have a recurrence if any new uterine fibroids develop in the future. The term does not necessarily mean that the exact same fibroids that were eliminated grow back.

Symptomatic fibroids: This term refers to uterine fibroid tumors that produce a significant adverse biological effect such as infertility, urinary incontinence, constipation, menorrhagia (prolonged and profuse uterine bleeding) or pain.

DNA Construct: A DNA construct, as this term is used herein is any DNA produced or synthesized in which there are two or more distinct elements. For example, the structural sequence of a gene when combined with a particular 5' UTR could constitute a construct.

Vector: A plasmid, phage, or other DNA sequence which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain a marker suitable for use in the identification of transformed cells. For example, markers may provide tetracycline or ampicillin resistance.

Expression vector: A vector which is capable of inducing the expression of the DNA that has been cloned into it after transformation into a host. The cloned DNA is usually placed under the control of (i.e., operably linked to) certain regulatory sequences such as promoters or enhancers. Promoter sequences may be constitutive, inducible or repressible.

Isolated: The term "isolated" refers to a molecule that has been removed from its native environment. For example, a protein or gene present in a living animal is not "isolated," but the same protein or gene separated from the materials of its natural state, e.g., purified by some biochemical procedure, is "isolated."

Substantially Pure: When the term "substantially pure" is used in reference to a molecule, it means that the concentration of the molecule has been increased relative to molecules associated with it in its natural environment, or the environment in which it was produced, found or synthesized. Naturally associated molecules include proteins, nucleic acids, lipids and sugars but generally do not include water, buffers, and reagents added to maintain the integrity or facilitate the purification of the molecule being purified. According to this definition, a substance may be at least 60%, 80%, 90%, 95% or 99% pure when considered relative to its contaminants.

Host: Any prokaryotic or eukaryotic cell that is the recipient of a replicable expression vector or cloning vector is the "host" for that vector. The term encompasses prokaryotic or eukaryotic cells that have been engineered to incorporate a desired gene into its chromosome or in its genome. Examples of cells that can serve as hosts are well known in the art, as are techniques for cellular transformation (see e.g. Sambrook et al., *Molecular Cloning: A Laboratory Manual*, 2nd ed. Cold Spring Harbor (1989)).

Promoter: A DNA sequence typically found in the 5' region of a gene, located proximal to the start codon. Transcription is initiated at the promoter. If the promoter is of the inducible type, then the rate of transcription increases in response to an inducing agent.

Operably linked: The term "operably linked" refers to genetic elements that are joined in such a manner that enables them to carry out their normal functions. For example, a gene is operably linked to a promoter when its transcription is under the control of the promoter and such transcription produces the protein normally encoded by the gene.

DETAILED DESCRIPTION OF THE INVENTION

I. Assays

Diagnostic assays for determining whether cells derived from a woman have the allelic form of HMGA2 associated with a predisposition for fibroid formation may be performed by PCR amplifying polynucleic acid that has been extracted from cells using methods well known in the art. Amplification may be performed using the primers and procedures described, for example, in Ishwad, et al., *Hum. Genet.* 99:103-105 (1997). The primers used therein are: 5'CCG ACT GCC CAA GGC ACT TT 3' (sense, SEQ ID NO:11) and 5' TCG CGG GTT GGG ATC AGG 3' (antisense, SEQ ID NO:12) but other primers based upon the known HMGA2 gene sequence may also be employed. PCR reactions may be performed in a small reaction volume, e.g., 25 µl, using for example: 10 mM Tris (pH 9.0), 50 mM KCl, 1.5 mM MgCl2, 0.01% Triton X-100 mM each dNTPs, 40 nM unlabeled primer, 0.5 unit Taq polymerase and 100-200 ng of genomic DNA. In cases where the PCR product will be analyzed by electrophoresis or by hybridization, it may be desirable for one of the primers to be end-labeled with $^{32}$P-ATP, e.g., using T4 polynucleotide kinase.

PCR reactions will involve repeated cycles of denaturation, annealing and elongation. For example, DNA may be denatured at 95° C. for 7 min. and subjected to 30 cycles of denaturation at 94° C. for 45 s, annealing at 68° C. for 45 s, strand elongation at 72° C. for 45 s and final elongation at 72° C. for 10 min. PCR products are preferably analyzed by sequencing using standard methodology. However, other methods of analysis are also possible. For example, Ishwad et al. uses an electrophoretic procedure in which PCR products are diluted 1:1 with loading buffer (95% deionized formamide, 20 mM EDTA, 0.025% xylene cynol, 0.025% bromophenol blue). The diluted (4 ml) samples are then heat denatured and subjected to electrophoresis through 7% polyacrylamide gels containing 5.6 M urea and 32% formamide for 3 h at 55° C. Finally, gels are exposed to X-ray film at −80° C. and allelic sizes are determined by direct comparison to an M13 sequencing ladder.

Alternatively, assays may be developed based upon hybridizations performed under stringent conditions using probes that bind only to a specific allelic sequence. The probes should be a minimum of 15 nucleotides in length and must cover at least a portion of the 5' untranslated region of HMGA2. Stringent conditions would typically involve hybridization at a temperature of 60-70° C. with a low salt concentration (e.g., 0.02 M to 0.15 M NaCl). Procedures for selecting and labeling probes as well as for carrying out hybridizations and analyzing results are well known in the art of molecular biology (see, e.g., Sambrook, et al., *Molecular Cloning: A Laboratory Manual*, Cold Spring Harbor Laboratory Press, Cold Spring Harbor, N.Y. (1989)).

II. Diagnostic Kits

The invention also includes diagnostic kits that can be used for performing assays to determine whether a woman carries an HMGA2 allele that predisposes her to the formation of uterine fibroids. A kit will comprise at least one container with one or more components needed to conduct the assay. For example, the container may include a primer necessary for a PCR based assay (e.g., having a sequence corresponding to that of SEQ ID NO:11 or 12) or a probe needed for a hybridization step. Typically, a kit will contain all of the components needed to perform a PCR amplification or a hybridization based assay (with the possible exception of some common laboratory reagents such as water, buffers salts etc.) along with instructions for performing the assay. Reagents for the sequencing of amplification products may also be included in kits. However since sequencing equipment may vary somewhat from laboratory to laboratory, these reagents will typically be omitted. The assay components in kits may either be ready for immediate use or they may be in a lyophilized or concentrated state, requiring reconstitution or dilution before use.

III. DNA Constructs, Recombinant Cells and Transgenic Animals

The invention includes DNA constructs that can be used to introduce the 27 TC repeat described herein into the 5' untranslated region of the HMGA2 gene of cells and to recombinant cells engineered to incorporate the DNA constructs into their genomic DNA or transformed with a vector containing the fibroid associated allele. Embryonic stem cells which have been engineered to contain an allelic form of HMGA2 associated with a predisposition to uterine fibroids (i.e., an allele having the 27 TC repeat in its 5' UTR, preferably between 400 and 800 nucleotides upstream of the HMGA2 ATG start codon) can be incorporated into a developing embryo and, ultimately, used to produce transgenic mice which may be studied by scientists interested in determining the mechanisms promoting fibroid growth or in evaluating drugs with potential use in the treatment of patients with fibroids. Both the transgenic mice per se and the assays in which they are used are also part of the invention.

A. DNA Constructs

DNA constructs can take essentially two different forms. First, constructs may take the form of an expression vector in which a promoter is operably linked to a region that encodes the HMGA2 sequence (either human or mouse) and includes between 50 and 1000 nucleotides of 5' untranslated sequence, preferably corresponding to regions found in wild type cells. These vectors may be used to transform cells to study the effect of the 5' UTR TC repeats (especially the 27 TC repeat) on HMGA2 translation and cell biology. Standard methods for making vectors of this type and for transforming host cells may be used and are well known in the art (see, e.g., Sambrook, et al., *Molecular Cloning: A Laboratory Manual*, Cold Spring Harbor Laboratory Press, Cold Spring Harbor, N.Y. (1989)).

DNA constructs may also be made for the purpose of introducing the fibroid-associated HMGA2 allele (27 TC repeats) into the 5' UTR of an endogenous HMGA2 gene (i.e., a gene normally found in a cell as opposed to having been recombinantly introduced) by homologous recombination. This entails essentially the same technology as has been used in other contexts for the production of "knockout" mice. Typically, constructs of this type will contain a short insertion region (e.g., 50-100 nucleotides long) in which the wild type sequence (i.e., the sequence normally found in the cell) is modified in some manner (e.g., to include a chosen TC repeat region). The insertion region is flanked by two targeting sequences that exactly match endogenous sequences on either side of the genomic site where the insertion region is to be located (in this case, regions from the HMGA2 gene). The targeting segment used in constructs may be derived from the sequences of the mouse HMGA2 gene (see SEQ ID NOs:9 and 10) and constructs can be made and tested using methods that are routine in the field of molecular biology (see, e.g., Sambrook, et al., *Molecular Cloning: A Laboratory Manual*, Cold Spring Harbor Laboratory Press, Cold Spring Harbor, N.Y. (1989)).

In addition, most constructs for homologous recombination will include a marker sequence that can be used in selecting host cells in which integration of constructs into the genome has occurred. The marker sequence will typically be an antibiotic resistance gene or other gene whose expression can be easily detected and which is not normally present in the host. The marker gene may be expressed in the host cell either as a result of its being operably linked to a promoter in the construct, or by coming under the control of a native gene promoter after genomic integration. In cases where it is part of the construct, the promoter should be selected based upon its having a high activity in the particular host cell undergoing homologous recombination. A typical example of a promoter suitable for use in mouse cells is the promoter of the phosphoglycerate kinase gene and the most preferred gene for use as a marker is the neomycin resistance gene (Neo). Cells which have integrated Neo into their genome and which are expressing this gene are resistant to G418. Thus, a simple means is provided for selecting recombinant cells.

In addition to a marker gene used for identifying cells that have undergone homologous recombination, the constructs of the present invention will typically include a gene that can be used for distinguishing between cells in which recombination has occurred at the correct locus and cells in which recombination has occurred elsewhere in the genome. Preferably, this "selection sequence" will consist of the HSV-thymidine kinase gene under the control of an appropriate promoter. The combination of a marker sequence for selecting all cells that have undergone homologous recombination (e.g., Neo) and a selection sequence for distinguishing site specific integration from random integration (e.g., thymidine kinase) has been termed "positive-negative selection" and details of both the procedure and the production of constructs appropriate for the procedure are well known in the art (see Capecchi, *TIG* 5:70 (1989); Mansour, et al., *Nature* 336:348 (1988); Thomas, et al., *Cell* 51:503 (1987); and Doetschman, et al., *Nature* 330:576 (1987)).

The DNA construct described above may be transfected directly into appropriate host cells or it may first be placed in a vector for amplification prior to transfection. Preferred vectors are those that are rapidly amplified in bacterial cells such as the pBluescript IISK vector (Stratagene, San Diego, Calif.) or pGEM 7 (Promega Corp., Madison, Wis.). DNA constructs may be either circular or linear. However, it is generally preferred that prior to transfection into host cells, circular constructs be linearized.

B. Host Cells Comprising DNA Constructs

The present invention encompasses cells which have been genetically engineered using the DNA constructs described above. This includes without limitation, cells from humans, rats, hamsters, mice, etc. In cases where transgenic animals are being made, the most preferred host cells are mouse embryonic stem (ES) cells. ES cells should be selected based upon their ability to integrate into and become part of the germ line of a developing embryo. Any ES cell line that has this characteristic may be used, e.g., the murine cell line D3 (ATCC Catalog No. CRL1934). After appropriate host cells have been chosen, they are cultured and prepared for DNA insertion using methods well-known in the art (see, e.g., Robertson, In *Teratocarcinomas and Embryonic Stem Cells: A Practical Approach*, E. J. Robertson, ed, IRL Press, Washington, D.C. (1987); Bradley, et al., *Current Topics in Devel. Biol.* 20:357-371 (1986); and Hogan, et al., *Manipulating the Mouse Embryo: A Laboratory Manual*, Cold Spring Harbor Laboratory Press, Cold Spring Harbor, N.Y. (1986)).

The introduction of constructs into host cells can be accomplished using any of a variety of methods such as electroporation, microinjection or calcium phosphate treatment. In the case of embryonic stem cells, the preferred method of insertion is electroporation. If the DNA construct has been inserted into a vector, it is preferred that the DNA be linearized prior to transfection. Linearization can be accomplished by digesting the DNA vector with a restriction endonuclease selected to cut outside of the construct sequence.

The screening of transfected cells can be carried out using several different methods. In cases where an antibiotic resistance gene has been used as a marker, cells can be cultured in the presence of antibiotic to identify recombinants. In cases where other types of markers are used, Southern hybridizations may be carried out using labeled probes specific for the marker sequence. Finally, if the marker gene encodes an enzyme whose activity can be detected (e.g., beta-galactosidase), enzymatic assays may be performed.

Although one may introduce a human HMGA2 fibroid-associated allele into the mouse genome at any position, in most cases it will be preferable to either replace all or part of an endogenous mouse allele or to modify the 5' UTR of an endogenous mouse allele. Thus, it will usually be advantageous not only to identify cells in which recombination has occurred, but also to distinguish specific recombination, i.e., integration at the proper genomic location, from random insertion events occurring elsewhere in the genome. To identify cells with proper integration, chromosomal DNA can be extracted from cells using standard methods and Southern hybridizations can be performed using probes designed to hybridize specifically to DNA derived from constructs. Alternatively, PCR amplification can be performed using primers that will only act in cells where homologous recombination has occurred or which will produce a distinctive product of known size from such cells.

One way to enrich preparations for recombinants modified at the HMGA2 5' UTR site is to incorporate an HSV-thymidine kinase gene into constructs at a position adjacent to the targeting segment. The construct is designed so that the HSV-tk gene is only transferred to the host cell genome when recombination does not occur at the proper genomic site. Because the HSV-tk gene makes cells susceptible to the drug gancyclovir, the exposure of recombinants to this drug will negatively select against cells in which random integration has occurred (see Mansour, et al., *Nature* 336:348 (1988)).

It will be appreciated that homologous recombination will result in the modification of one HMGA2 allele much more frequently than in the disruption of both alleles. If one desires to produce cells that are modified at both alleles, it will probably be necessary to conduct a second round of homologous recombination on cells that have already been selected as having one allele modified. In the second round of transfection, a marker should be used that is different from the marker used in producing the initial recombinants. For example, if a neomycin resistance gene was used to produce cells with one modified allele, beta-galactosidase may be used as a marker in the second construct. Screening for cells that have incorporated DNA at the desired genomic site may be carried out as described above.

C. Development of Transgenic Animals

Embryonic stem cells engineered to contain a specific HMGA2 allele and produced by homologous recombination as described above may be used to make transgenic animals. In particular, animals may be produced which contain at least one HMGA2 allele with the 27 TC repeat region that has been associated with an increased risk of fibroid formation. Animals may also be produced that have other HMGA2 alleles or in which both alleles are modified. The methodology needed to make such animals can be adapted to any non-human animal such as hamsters, rats or, preferably, mice.

The first step in the making of transgenic animals is to produce ES cells modified by homologous recombination so that they have the desired alleles. This may be accomplished using the procedures described above or other similar procedures. The next step is to incorporate the mutant embryonic stem cells into an embryo. The preferred method for accomplishing this is by microinjection into an embryo at the blastocyst stage of development. In mice, blastocysts at about 3.5 days of development may be obtained by perfusing the uterus of pregnant animals (Bradley, in: *Teratocarcinomas and Embryonic Stem Cells: A Practical Approach*, Robertson, E. D., IRLP Press, Washington, D.C. (1987)). Preferred blastocysts are male and have genes coding for a coat color or another phenotypic marker that is different from the corresponding marker encoded by the stem cell genes. In this way, offspring are produced that can be easily screened for the presence of altered HMGA2 alleles. For example, if the ES cell line carries the gene for a white coat, the embryo selected will, preferably, carry the gene for a black or brown coat and offspring carrying a chosen allele should have mosaic coats.

After the embryonic stem cells have been incorporated into the blastocyst, the chimeric embryo is implanted into the uterus of a pseudopregnant animal. Such animals may be prepared by mating females with vasectomized males of the same species. The pseudopregnant stage of the female is important for successful implantation and will vary from species to species. For mice, females about two to three days pseudopregnant should typically be used.

After chimeric embryos have been implanted into pseudopregnant animals, they are allowed to develop to term and offspring are then screened for the presence of the chosen HMGA2 allele. In cases where a phenotype selection strategy has been employed, e.g., based upon coat color as described above, initial screening may be accomplished by simple inspection of animals for mosaic coat color or some other readily apparent phenotypic marker. In addition, or as an alternative, chromosomal DNA may be obtained from the tissue of offspring, e.g., from the tail tissue of mice, and screened for the presence of a modified nucleotide sequence at the 5' UTR of the HMGA2 gene locus using Southern blots and/or PCR amplification.

Once offspring have been identified carrying the desired HMGA2 allele, they can be interbred to produce homozygous animals. Heterozygotes may be identified using Southern blots or PCR amplification as described above. Homozygotes may be identified by Southern blotting of equivalent amounts of genomic DNA obtained from the offspring of crossed heterozygotes, from the heterozygotes themselves, and from wild-type animals. Probes should be designed to bind to a portion of the HMGA2 gene sequence present in all animals and the presence of mutant alleles can be determined by the relative position of bands in autoradiographs. Alternatively, analysis may be performed based upon the relative sizes of PCR amplification products.

Homozygous transgenic animals may be interbred to provide a continual supply of animals that can be used in identifying biological characteristics or pathologies dependent upon the presence of the selected HMGA2 allele (preferably the 27 TC repeat allele) and in cases where a predisposition to fibroid formation is identified, in evaluating drugs in the assays described below.

D. Assay Methods Utilizing Transgenic Animals

Transgenic animals found to have a predisposition to the development of uterine fibroids can be used to help in the identification and development of new therapeutic agents. Specifically, these animals may be administered test compounds either prior to or after fibroids develop in order to determine whether the compounds have an effect on occurrence (the number of fibroids that form and the rapidity at which they form) or severity (the size of tumors). The assays may involve either screening multiple compounds or they may entail a more thorough study of one or more selected compounds. In the latter case, assays will typically involve utilizing transgenic animals divided into a variety of experimental groups. For example, animals may be placed in treatment group that receives the compound being tested and a control group that does not. For comparison, normal nontransgenic mice may also be included in a study. In general, it is desirable to use sufficient animals in each group to assure that statistically significant results can be obtained. Apart from the compound tested, parameters that may be varied include the duration of drug delivery, dosage, route of administration or dosage form. It may also be desirable to test combinations of agents or to test animals at various ages or physiological states.

All references cited herein are fully incorporated by reference in their entirety. Having now fully described the invention, it will be understood by those of skill in the art that the invention may be practiced within a wide and equivalent range of conditions, parameters and the like, without affecting the spirit or scope of the invention or any embodiment thereof.

---

What is claimed is:

1. A method of assessing the increased risk of a woman of forming uterine fibroids, comprising:
   a) determining in a nucleic acid sample from the woman if the genome of said woman includes an allelic form of an HMGA2 gene sequence encoding the protein of either SEQ ID NO: 1, SEQ ID NO: 2 or SEQ ID NO: 3, wherein said HMGA2 gene is characterized by a repeat sequence (TC)n where n=27, located in the 5' untranslated region of said gene; and
   b) concluding that said woman is at increased risk of developing uterine fibroids if said allelic form, characterized by a repeat sequence (TC)n where n=27, is present.

2. The method of claim 1, wherein said repeat sequence is located 400-800 nucleotides 5' to the ATG translation start codon of said HMGA2 gene as shown in SEQ ID NOs:4-7.

3. The method of claim 1, wherein said repeat sequence is found 500-700 nucleotides 5' to the ATG translation start of said HMGA2 gene as shown in SEQ ID NOs:4-7.

4. The method of claims 1, wherein the determination of step a) includes an amplification of the region of said HMGA2 gene comprising said repeat sequence by PCR.

5. The method of claim 4, wherein said region comprises at least 54 sequential nucleotides located in the region 400-800 nucleotides 5' to the ATG start codon of said HMGA2 gene.

6. The method of claim 5, wherein the PCR amplification produces a product 54-400 nucleotides in length.

7. The method of claim 4, wherein said method further comprises either:
   a) sequencing the amplification product produced;
   b) analyzing the size of the amplification product; or
   c) analyzing the amplification product by hybridization under stringent conditions.

8. The method of claim 7, wherein said PCR amplification is performed using primers having the sequences of SEQ ID NO: 11 and SEQ ID NO: 12.

9. The method of claim 1, wherein said method consists of:
 a) determining if the genome of said woman includes an allelic form of an HMGA2 gene sequence encoding the protein of SEQ ID NO:1, wherein said HMGA2 gene is characterized by a repeat sequence (TC)11 where n=27, located in the 5' untranslated region of said gene; and
 b) concluding that said woman is at increased risk of developing uterine fibroids if said allelic form, characterized by a repeat sequence $(TC)_n$ where n=27, is present.

10. The method of claim 9, wherein said repeat sequence is located 400-800 nucleotides 5' to the ATG translation start codon of said HMGA2 gene.

11. The method of claim 9, wherein said repeat sequence is found 500-700 nucleotides 5' to the ATG translation start of said HMGA2 gene.

12. The method of claim 9, wherein the determination of step a) includes an amplification of the region of said HMGA2 gene comprising said repeat sequence by PCR.

13. The method of claim 1, wherein said method consists of:
 a) determining if the genome of said woman includes an allelic form of an HMGA2 gene sequence encoding the protein of SEQ ID NO:2, wherein said HMGA2 gene is characterized by a repeat sequence $(TC)_n$ where n=27, located in the 5' untranslated region of said gene; and
 b) concluding that said woman is at increased risk of developing uterine fibroids if said allelic form, characterized by a repeat sequence $(TC)_n$ where n=27, is present.

14. The method of claim 13, wherein said repeat sequence is located 400-800 nucleotides 5' to the ATG translation start codon of said HMGA2 gene.

15. The method of claim 13, wherein said repeat sequence is found 500-700 nucleotides 5' to the ATG translation start of said HMGA2 gene.

16. The method of claim 13, wherein the determination of step a) includes an amplification of the region of said HMGA2 gene comprising said repeat sequence by PCR.

17. The method of claim 1, wherein said method consists of:
 a) determining if the genome of said woman includes an allelic form of an HMGA2 gene sequence encoding the protein of SEQ ID NO:3, wherein said HMGA2 gene is characterized by a repeat sequence $(TC)_n$ where n=27, located in the 5' untranslated region of said gene; and
 b) concluding that said woman is at increased risk of developing uterine fibroids if said allelic form, characterized by a repeat sequence $(TC)_n$ where n=27, is present.

18. The method of claim 17, wherein said repeat sequence is located 400-800 nucleotides 5' to the ATG translation start codon of said HMGA2 gene.

19. The method of claim 17, wherein said repeat sequence is found 500-700 nucleotides 5' to the ATG translation start of said HMGA2 gene.

20. The method of claim 17, wherein the determination of step a) includes an amplification of the region of said HMGA2 gene comprising said repeat sequence by PCR.

* * * * *